United States Patent [19]
Anderson et al.

[11] Patent Number: 5,676,131
[45] Date of Patent: Oct. 14, 1997

[54] SYSTEM FOR PROTECTING SAMPLE LINE IN RESPIRATORY GAS ANALYZER

[75] Inventors: David M. Anderson, Lino Lakes; Steven D. James, Edina; Thor A. Larson, Hugo, all of Minn.

[73] Assignee: Medical Graphics Corporation, St. Paul, Minn.

[21] Appl. No.: 678,347

[22] Filed: Jul. 11, 1996

[51] Int. Cl.[6] .................................................. A61M 16/00
[52] U.S. Cl. .................. 128/204.22; 128/204.23; 128/202.22
[58] Field of Search .................. 128/202.22, 204.22, 128/204.23; 364/413.01, 413.02, 413.03

[56] References Cited

U.S. PATENT DOCUMENTS

| | | |
|---|---|---|
| 4,197,858 | 4/1980 | Osborn . |
| 4,446,869 | 5/1984 | Knodle . |
| 4,546,778 | 10/1985 | Sullivan . |
| 4,550,726 | 11/1985 | McEwen ............... 128/202.22 |
| 4,592,368 | 6/1986 | Ricciardelli et al. . |
| 4,799,374 | 1/1989 | Bossart et al. . |
| 4,924,860 | 5/1990 | Larsen et al. . |
| 4,958,075 | 9/1990 | Mace et al. . |
| 5,038,773 | 8/1991 | Norlien et al. . |
| 5,209,761 | 5/1993 | Ivester et al. . |
| 5,231,991 | 8/1993 | Nelson . |

Primary Examiner—Vincent Millin
Assistant Examiner—Robert Wieland
Attorney, Agent, or Firm—Haugen and Nikolai, P.A.

[57] ABSTRACT

A method and apparatus is described for preventing contamination of a gas analyzer of respiratory gas exchange analyzing equipment due to a patient's saliva. The method involves determining a resistance value of the inspired respiratory gas flow in a sample line leading to the gas analyzer. This is determined by calculating the absolute pressure in the line at the gas analyzer. The pressure difference from atmospheric pressure is then divided by the sample flow rate to obtain a resistance value. A microprocessor in the equipment compares the calculated resistance of the flow with a previously stored reference threshold resistance. If the calculated resistance exceeds the predetermined threshold, the microprocessor sends a signal to a vacuum pump used to draw the respiratory gases through the gas analyzer. The vacuum pump is immediately shut down when the calculated resistance exceeds the predetermined resistance threshold and, hence, any saliva in the sample line is not drawn into the gas analyzer.

4 Claims, 2 Drawing Sheets ns/n# 5,676,131

SYSTEM FOR PROTECTING SAMPLE LINE IN RESPIRATORY GAS ANALYZER

BACKGROUND OF THE INVENTION

I. Field of Invention

The present invention relates generally to electronic medical instrumentation for a respiratory gas exchange system and more particularly to a method and apparatus which protects the respiratory gas analyzer of the electronic medical instrumentation from fluid build up during the patient's assessment.

II. DISCUSSION OF THE PRIOR ART

Respiratory gas exchange systems use monitors to assess the performance of the heart and lungs. These devices typically have a plurality of gas sensors connected to a sample line for measuring the percentage concentration of discrete gases in an air mixture being exhaled. U.S. Pat. No. 4,463,764 to Anderson, et al. describes a cardiopulmonary exercise device, one type of a respiratory gas exchange system. It includes a pneumotach, in the form of a patient mouthpiece incorporating pitot tubes, coupled by tubing to a differential pressure sensor used in computing inspired and expired respiratory flow. The gas sensors and the pressure sensor each provide an analog output to a microprocessor based waveform analyzer. The microprocessor is programmed to process the sensor derived information for providing a variety of cardiopulmonary performance parameters used by physicians for evaluating the physiologic condition of the patient.

As those skilled in the art appreciate, saliva and condensation can build up in the sample line and unless properly addressed, can be drawn into the gas analyzer disrupting the measurements by adding a phase delay variation. Once liquid has entered the analyzer, the measurements are no longer reliable. The system must be shut down and the liquid must be removed from the analyzer. Cleaning the analyzer is difficult and time consuming.

In an effort to address the problem of liquid entering the gas analyzer, prior art devices have introduced a waste trap at the mouthpiece or in the sample line between the mouthpiece and the analyzer. When the level of moisture in the waste trap reaches a pre-determined limit, it is automatically purged. For example, U.S. Pat. No. 5,231,991 to Nelson uses a waste trap in the sample line for collecting moisture. A pump is used to draw the gas sample through a $CO_2$ analyzer with a differential pressure transducer sensing the pressure difference across the trap. When the resistance increases, the device is programmed to automatically shut off the pump.

Other prior art devices, such as that in U.S. Pat. No. 5,209,761 to Ivester, uses a waste trap incorporating electrodes for detecting when the level of liquid in the trap reaches a pre-determined threshold. A signal is generated for turning on a vacuum for draining the trap before it can reach a level where the moisture would enter the equipment downstream from the trap. Another prior art device is found in U.S. Pat. No. 4,958,075 to Mace. This device uses a moisture trap that is incorporated in the flow line between the sample device and a pump/pressure monitoring control unit. The trap removes moisture from the gases being drawn to the vacuum pump.

The invention described in U.S. Pat. No. 4,924,860 to Larsen uses a filter element that creates a high resistance when wetted by moisture in the waste trap. A controller senses the high resistance and turns off the pump drawing the respiratory gas through the line. Another prior art device is shown in U.S. Pat. No. 4,799,374 to Bossart. In this device a valve is closed to block the fluid flow if the liquid level in the trap reaches a pre-determined threshold.

While these devices use various methods for stopping the flow of moisture into the sample line, they all require the use of a waste trap. However, the use of a waste trap will not prevent saliva from entering the gas analyzer. For example, if a patient does not use care in removing the mouthpiece during a test procedure, the waste trap may become tilted, letting saliva run out of the trap and enter the sample line. Furthermore, a waste trap increases the dead space in the sample line circuit which increases the response time, reduces the overall frequency response and decreases the accuracy of the system.

Therefore, what is needed is a more direct way to sense liquid build-up in a sample line in a respiratory gas exchange system that does not use a waste trap. In response to the sensed event, the system should be rapidly turned off to avoid drawing this liquid into the gas analyzer.

SUMMARY OF THE INVENTION

The present invention involves a method and apparatus for protecting a respiratory gas exchange system, such as found in a cardiopulmonary exercise test system or in a nutritional assesment system, from contamination by saliva. In a cardiopulmonary exercise test system, a patient's pulmonary performance during the course of an exercise regimen is evaluated. The patient on the treadmill has a mouthpiece through which he or she breaths. The mouthpiece is connected by a sample line to a gas analyzer for determining the oxygen and $CO_2$ concentration in a respiratory gas sample. A vacuum pump draws the respiratory gas sample through the analyzer. A flow meter is located in the sample line to measure the rate of flow of the respiratory gas mixture. An absolute pressure sensor is located at the gas analyzer to measure the pressure in the sample line as it exits the analyzer.

The microprocessor is programmed to compute the resistance R of the sample line in accordance with the following equation where:

$$R = \frac{\text{Pressure}_{atmosphere} - \text{Pressure}_{gas\ analyzer}}{\text{Flow Rate}_{Gas\ Sample}}$$

A resistance threshold value is programmed into the microprocessor. When the resistance exceeds the threshold level, the vacuum pump is automatically shut down by the microprocessor thus preventing saliva from entering the respiratory gas analyzer.

The primary object of the present invention is to protect the gas analyzer in respiratory exchange gas systems from saliva build up without having the increased dead space of a waste trap.

Another object of the present invention is to provide a method to assess a patient's pulmonary performance which includes immediately turning off the vacuum pump drawing the respiratory gas into the gas analyzer when the presence of saliva is sensed in the sample line.

Still another object of the present invention is to use a flow meter located in the sample line circuit for determining the oxygen and $CO_2$ concentration in the gas sample drawn through the analyzers and which sends a signal to the microprocessor that saliva will be drawn through if the system is not shut down.

A further object of the present invention is to prevent saliva from entering the gas analyzer in a respiratory gas exchange analyzing system when the patient being assessed removes the mouthpiece during the assessment period.

DESCRIPTION OF THE DRAWINGS

The foregoing features, objects and advantages of the invention will become apparent to those skilled in the art from which the following detailed description of a preferred embodiment in which.

DESCRIPTION OF THE PREFERRED EMBODIMENT

Figure 1:
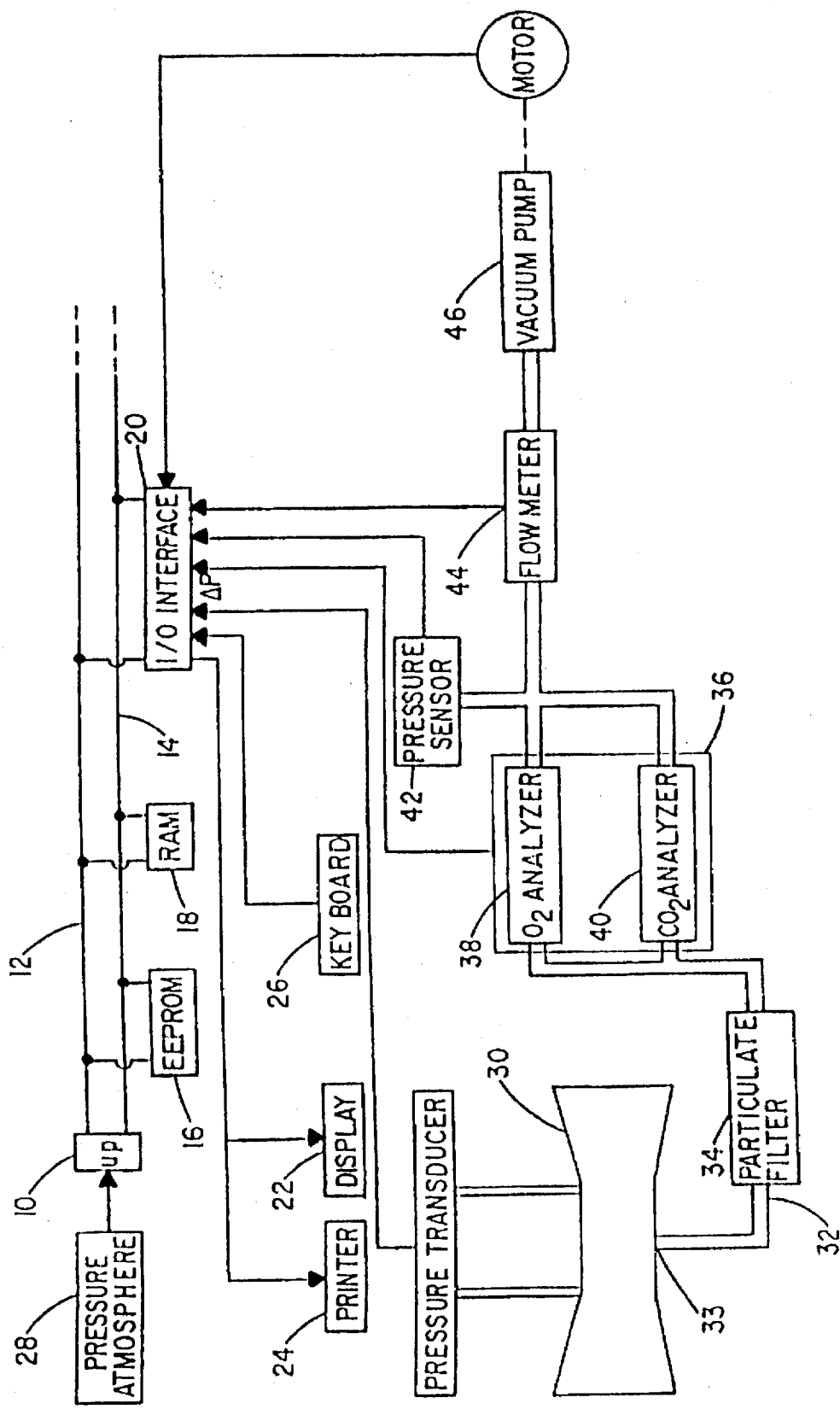
FIG. 1 is a block diagram of the portion of the cardiopulmonary performance analyzing equipment used in carrying out the method of the invention.

The present invention is for use with respiratory gas exchange systems such as a cardiopulmonary exercise system or a nutritional assesment system. One such cardiopulmonary exercise system is shown and described in U.S. Pat. No. 4,463,764 to Anderson et al. FIG. 1, depicts the type of waveform analyzer described in the Anderson et al., '764 Patent includes microprocessor 10 having an address bus 12 and a data bus 14 for connecting the microprocessor to an EEPROM memory 16, a RAM memory 18 and an I/O interface module 20. The EEPROM memory 16 is used to store the various constants necessary for carrying out certain calculations as well as a software program executable by the microprocessor 10. The RAM memory 18 is a read/write memory used to store operands, partial results and other data. The I/O interface module 20 may include an analog to digital (A/D) converter along with the necessary buffers and drivers for providing inputs to the microprocessor 10 over the data bus 14 and for feeding information to one or more output devices, such as a display monitor 22 and a hard copy printer 24. Alternatively, the A/D converter may be part of the microprocessor 10. Data can be entered into the microprocessor, via a keyboard 26, in a conventional fashion well known to those skilled in the art.

The respiratory gas exchange system equipment is also shown in FIG. 1. A mouthpiece 30, preferably a pneumotach mouthpiece like that shown in the Norlien, et al. U.S. Pat. No. 5,038,773, is coupled to the gas analyzer 36 via a sample line 32. an oxygen analyzer 38 and a $CO_2$ analyzer 40 are located at the gas analyzer 36. As can be appreciated by those of skill in the art, a conventional particulate filter and conventional gas dryer 34 may be located in the sample line prior to the gas analyzer 36. A pressure sensor 42 is located adjacent the gas analyzer 36 for measuring the pressure of the respiratory gas in the sample line 32. Pressure sensor 42 may also be used to measure ambient pressure. A flow meter 44, which may be a mircobridge sensor or a hot wire type and may include its own filter, is also located in the sample line 32. The flow meter provides an analog signal to the I/O interface 20 representing the volume rate of flow or the mass rate of flow of respiratory gas through the sample line 32. A vacuum pump 46 is coupled downstream from the analyzer 36 for drawing the respiratory gas from a port 33 in the mouthpiece 30, through the sample line 32 and then through the analyzer 36.

The respiratory gas exchange system equipment is controlled by the microprocessor 10 which receives inputs from the flow meter 44 and the pressure sensor 42. If the pressure sensor 42 is not used to measure ambient pressure, a pressure sensor 28 may be built into the equipment for providing an atmospheric pressure reference to the microprocessor so that absolute pressure can be determined. Alternatively, an atmospheric pressure value can be manually entered via the keyboard.

The microprocessor 10 is programmed to calculate the resistance in the sample line 32 and to compare it with a predetermined flow reference threshold level stored in the microprocessor at the time of manufacture to determine whether saliva has entered the line.

Figure 2:
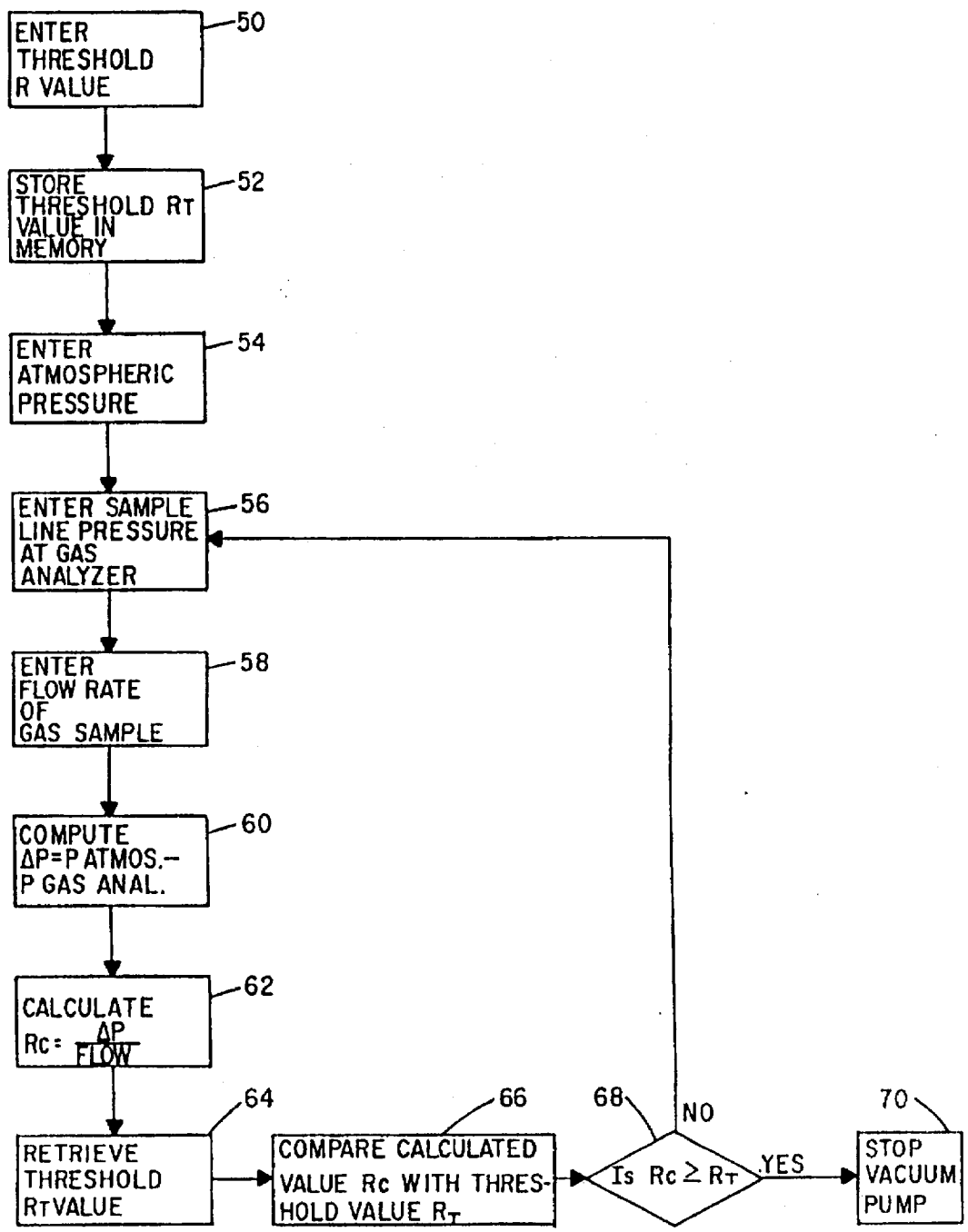
FIG. 2 is a software flow diagram of the major steps in carrying out the method of the present invention and useful in writing a program for the microprocessor whereby the method can be implemented.

With reference now to FIG. 2, the steps employed in this method for protecting the respiratory gas analyzer from saliva will be explained. First, the reference threshold level for the flow resistance in the sample line is entered into the memory 16 (indicated by blocks 50 and 52) at the time of manufacture. The keyboard 26, pressure sensor 42 or the on-board sensor 28 is used to enter the atmospheric pressure in the memory at the time the patient is to be evaluated (block 54). Next, the various sensors measure the conditions and send the information to the microprocessor 10. More specifically, the pressure at the output of the gas analyzer 36 is measured and this is stored in the memory (block 56). The flow rate of the respiratory gas flow in the sample line is determined by flow meter 44. A digitized value of sample line flow is sent to the memory of the microprocessor 10 (block 58). As indicated in block 60 of the flow chart of FIG. 2, the microprocessor 10 determines the pressure drop:

$$\Delta P = \text{Pressure}_{atmosphere} - \text{Pressure}_{gas\ analyzer}$$

The $\Delta P$ value is stored and the microprocessor 10 then calculates the flow resistance (block 62) using the following formula:

$$R = \frac{\Delta P}{\text{Flow Rate}_{gas\ sample}}$$

The microprocessor 10 then retrieves the reference threshold R value previously stored in the memory 16 at the factory (block 64) and compares the calculated resistance value with the threshold value (block 66). If the calculated resistance value is less than the threshold value it is indicated that no saliva has entered the sample line 32 and the patient assessment can continue. The microprocessor 10 then continuously repeats the steps reflected in blocks 56 through 66 in FIG. 2. A new $\Delta P$ and a new R of the sample line is calculated on each iteration. The new calculated R value is compared with the threshold value. If the test at block 68 establishes that the calculated R equals or exceeds the threshold value, it is concluded that salvia has entered the sample line 32 to cause the increase in flow resistance. The microprocessor 10 then sends a signal to the vacuum pump 46 to shut it off as indicated by block 70. Because the pump 46 shuts down, saliva will not be drawn into the gas analyzer 36. The sample line 32 must be cleaned or replaced before the patient assessment is resumed.

This invention has been described here in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. In a respiratory gas exchange system of the type including a patient mouthpiece having a sampling port coupled by a sample line in circuit with a gas analyzer and a vacuum pump, the vacuum pump drawing respiratory gases from said mouthpiece through said sample line and into said gas analyzer, a method for precluding a patient's saliva from reaching the gas analyzer, said method comprising the steps of:

a) measuring the rate of flow of respiratory gases in the sample line;

b) measuring the pressure in said sample line;

d) comparing the computed flow resistance value with a predetermined reference threshold;

e) repeating steps a)–d) until said computed flow resistance value exceeds said predetermined reference threshold; and f) shutting off the vacuum pump when the computed flow resistance value exceeds the predetermined reference threshold.

2. The method of claim 1 and further comprising the steps of repeating steps a–e until said resistance exceeds said threshold resistance value and automatically shutting down said pump when said resistance value exceeds said threshold resistance value.

3. In a gas exchange system analyzer of the type having a microprocessor based waveform analyzer including a memory for storing a program of instructions and operands, a sample line extending from a mouthpiece to a respiratory gas analyzer, a flow meter located in said sample line and coupled to said waveform analyzer for providing input thereto proportional to the volume rate of sample flow of respiratory gases in the sample line, a pressure sensor located adjacent said gas analyzer for sensing pressure of said sample flow in said gas analyzer and a pump for drawing said respiratory gases through said sample line and said respiratory gas analyzer, a method for determining the presence of saliva in the sample line, said method comprising the steps of:

a. entering into said memory a reference threshold sample resistance value;

b. sensing a first pressure value at the pressure sensor;

c. storing said first pressure in said memory;

d. computing a resistance value of said sample flow, using a value of atmospheric pressure, said first pressure and said volume rate of flow of said respiratory gases by using the formula:

$$\text{Resistance} = \frac{\text{Pressure}_{atmosphere} - \text{Pressure}_{gas\ analyzer}}{\text{Flow Rate}_{Gas\ Sample}}$$

and e. comparing said resistance value with said threshold resistance value.

4. An apparatus for protecting a sample line and a respiratory gas analyzer from saliva build up in a respiratory gas exchange system, said apparatus comprising:

a. a pneumotach mouthpiece;

b. a sample line circuit having a first end and a second end, said sample line coupled at said first end to said pneumatach mouthpiece;

c. a gas analyzer coupled to said sample line circuit;

d. a flow meter coupled to said sample line circuit, said flow meter measuring flow of respiratory gases flowing in said sample line;

e. a pressure sensor located adjacent said gas analyzer, said pressure sensor sensing the pressure of the sample line at said gas analyzer;

f. a vacuum pump coupled to said second end of said sample line, said vacuum pump drawing said respiratory gases through said sample line and said gas analyzer; and g. a controller for determining saliva build up in said sample line by analyzing inputs from said pressure sensor at said gas analyzer and said flow meter, said controller programmed to shut down said vacuum pump when a pre-determined saliva build up threshold is met.

* * * * *